US009759733B1

(12) United States Patent
Callahan

(10) Patent No.: US 9,759,733 B1
(45) Date of Patent: Sep. 12, 2017

(54) MASS PRODUCED, LOW COST, PORTABLE TEST KIT FOR THE DETECTION AND IDENTIFICATION OF NARCOTICS

(71) Applicant: Michael D. Callahan, Englewood, CO (US)

(72) Inventor: Michael D. Callahan, Englewood, CO (US)

(*) Notice: Subject to any disclaimer, the term of this patent is extended or adjusted under 35 U.S.C. 154(b) by 27 days.

(21) Appl. No.: 15/094,825

(22) Filed: Apr. 8, 2016

(51) Int. Cl.
| G01N 33/94 | (2006.01) |
| G01N 21/78 | (2006.01) |
| G01N 1/10 | (2006.01) |
| G01N 1/04 | (2006.01) |
| G01N 1/02 | (2006.01) |
| G01N 21/77 | (2006.01) |

(52) U.S. Cl.
CPC ........... G01N 33/9486 (2013.01); G01N 1/04 (2013.01); G01N 1/10 (2013.01); G01N 21/78 (2013.01); G01N 33/946 (2013.01); G01N 33/948 (2013.01); G01N 2001/028 (2013.01); G01N 2021/7759 (2013.01)

(58) Field of Classification Search
CPC .............................. G01N 21/78; G01N 33/94
USPC ........... 422/400, 411, 418, 425, 430; 436/92
See application file for complete search history.

(56) References Cited

U.S. PATENT DOCUMENTS

| 3,329,486 | A | * | 7/1967 | Rupe ...................... G01N 33/52 |
| | | | | 422/420 |
| 3,616,251 | A | * | 10/1971 | Linoli ..................... C12Q 1/00 |
| | | | | 422/404 |
| 3,713,779 | A | | 1/1973 | Sirago et al. |
| 3,748,098 | A | | 7/1973 | Dutch |
| 3,770,383 | A | * | 11/1973 | Price ................. G01N 33/543 13 |
| | | | | 422/425 |
| 3,915,639 | A | | 10/1975 | Friedenberg |
| 3,954,412 | A | * | 5/1976 | Ogawa .................. G01N 33/64 |
| | | | | 422/420 |
| 3,955,926 | A | | 5/1976 | Fischer |
| 3,972,992 | A | | 8/1976 | Cleeland et al. |
| 4,110,078 | A | | 8/1978 | Zelonis |
| 4,196,167 | A | | 4/1980 | Olsen |
| 4,288,344 | A | | 9/1981 | Reiss |
| 4,320,086 | A | | 3/1982 | Reiss |
| 4,752,448 | A | | 6/1988 | Wells |
| 4,771,005 | A | | 9/1988 | Spiro |
| 4,786,595 | A | * | 11/1988 | Arai .......................... C12Q 1/26 |
| | | | | 422/421 |
| 4,806,487 | A | | 2/1989 | Akers |
| 4,812,413 | A | * | 3/1989 | Glattstein ............. G01N 33/946 |
| | | | | 422/413 |
| 4,816,415 | A | | 3/1989 | Akers |
| 4,840,912 | A | | 6/1989 | Glattstein |
| 4,877,580 | A | * | 10/1989 | Aronowitz ............. G01N 33/52 |
| | | | | 356/42 |
| 4,965,047 | A | | 10/1990 | Hammond |
| 5,013,669 | A | * | 5/1991 | Peters, Jr. ......... G01N 33/54306 |
| | | | | 435/7.1 |
| 5,039,618 | A | * | 8/1991 | Stone ...................... G01N 33/84 |
| | | | | 422/537 |
| 5,212,060 | A | * | 5/1993 | Maddox ................ B01L 3/5023 |
| | | | | 422/401 |
| 5,260,195 | A | * | 11/1993 | Azhar .................... C12N 11/08 |
| | | | | 422/400 |
| 5,278,075 | A | * | 1/1994 | Stone ...................... G01N 33/84 |
| | | | | 422/412 |
| 5,334,502 | A | * | 8/1994 | Sangha .............. A61B 10/0051 |
| | | | | 422/412 |
| 5,457,054 | A | | 10/1995 | Geisinger |
| 5,523,051 | A | | 6/1996 | Gibson |
| 5,753,513 | A | | 5/1998 | Amisar |
| 5,858,797 | A | * | 1/1999 | Evtodienko ............ G01N 31/22 |
| | | | | 422/421 |
| 6,133,040 | A | | 10/2000 | Glattstein |
| 6,150,178 | A | * | 11/2000 | Cesarczyk ......... A61B 10/0045 |
| | | | | 422/412 |
| 6,420,181 | B1 | * | 7/2002 | Novak .................... G01N 31/22 |
| | | | | 210/658 |
| 6,514,769 | B2 | * | 2/2003 | Lee ....................... B01L 3/5023 |
| | | | | 422/110 |
| 6,514,773 | B1 | * | 2/2003 | Klein .................... C07D 451/02 |
| | | | | 435/4 |
| 6,565,808 | B2 | * | 5/2003 | Hudak .................. B01L 3/5023 |
| | | | | 422/411 |
| 6,663,831 | B2 | * | 12/2003 | Konecke ............. A61B 10/0045 |
| | | | | 422/417 |
| 6,709,633 | B2 | * | 3/2004 | Etes ..................... G01N 33/558 |
| | | | | 422/412 |

(Continued)

FOREIGN PATENT DOCUMENTS

| WO | 8402397 A1 | 6/1984 |
| WO | 8909395 A1 | 10/1989 |

OTHER PUBLICATIONS

Alliston, G. V. et al, Analyst 1972, 97, 263-265.*
Kidwell, D. A. et al, Forensic Science International 1997, 84, 75-86.*
Tsumura, Y. et al, Forensic Science International 2005, 155, 158-164.*
Haddoub, R. et al, New Journal of Chemistry 2011, 35, 1351-1354.*
Musile, G. et al, Analytical Methods 2015, 7, 8025-8033.*
World drug report 2014: Amphetamine-type stimulants; http://www.unodc.org/wdr2014/en/ats.html.

(Continued)

Primary Examiner — Arlen Soderquist
(74) Attorney, Agent, or Firm — Shifrin Patent Law; Dan Shifrin

(57) ABSTRACT

A highly portable, paper and swab-based detection kit is provided for identifying Amphetamine, Cannabis, Cocaine, Heroin, selected synthetic Cannabinoid, and amphetamine based Cathinone type stimulants, and cannabis consumable products. A method of mass manufacture providing low cost kits with long term commercial shelf life and a method of use are also provided.

45 Claims, 2 Drawing Sheets

(56) References Cited

U.S. PATENT DOCUMENTS

| | | | |
|---|---|---|---|
| 6,787,366 B1* | 9/2004 | Novak | G01N 31/22 210/634 |
| 6,821,788 B2* | 11/2004 | Cesarczyk | A61B 10/0045 422/412 |
| 7,114,403 B2* | 10/2006 | Wu | A61B 10/0051 73/864.72 |
| 7,244,392 B1* | 7/2007 | Konecke | A61B 10/007 422/408 |
| 7,319,032 B2* | 1/2008 | Bohannon | G01N 33/54393 422/412 |
| 7,374,946 B2 | 5/2008 | Glattstein | |
| 7,384,599 B2 | 6/2008 | Brewer | |
| 7,455,813 B2* | 11/2008 | Anderson | G01N 33/94 422/411 |
| 7,544,324 B2* | 6/2009 | Tung | A61B 10/0045 422/504 |
| 7,879,293 B2* | 2/2011 | Niedbala | A61B 10/0045 422/408 |
| 7,958,792 B2* | 6/2011 | Peng | G01N 1/02 73/864.71 |
| 8,124,420 B2 | 2/2012 | Amisar | |
| 8,770,049 B2* | 7/2014 | Pelssers | A61B 10/0045 422/411 |
| 2001/0046710 A1* | 11/2001 | Cutler | G01N 31/22 436/24 |
| 2002/0001854 A1* | 1/2002 | Lee | B01L 3/5023 436/518 |
| 2002/0072124 A1* | 6/2002 | Khan | G01N 33/54366 436/95 |
| 2002/0106809 A1* | 8/2002 | Cesarczyk | A61B 10/0045 436/165 |
| 2002/0146346 A1* | 10/2002 | Konecke | A61B 10/0045 422/417 |
| 2002/0173047 A1* | 11/2002 | Hudak | B01L 3/5023 436/178 |
| 2003/0022392 A1* | 1/2003 | Hudak | B01L 3/502 436/518 |
| 2003/0064526 A1* | 4/2003 | Niedbala | A61B 10/0045 436/165 |
| 2004/0184954 A1* | 9/2004 | Guo | A61B 10/0051 422/400 |
| 2004/0237674 A1* | 12/2004 | Wu | A61B 10/0051 73/864 |
| 2005/0008538 A1* | 1/2005 | Anderson | G01N 33/94 422/411 |
| 2005/0130312 A1 | 6/2005 | Glattstein | |
| 2005/0277202 A1* | 12/2005 | Fleming | G01N 33/558 436/514 |
| 2006/0286606 A1* | 12/2006 | Oliver | B01L 9/54 435/7.1 |
| 2007/0128070 A1* | 6/2007 | Wu | A61B 10/0051 422/400 |
| 2008/0044310 A1* | 2/2008 | Haas | G01N 21/77 422/400 |
| 2008/0254550 A1* | 10/2008 | Nathaniel | A61B 10/0045 436/165 |
| 2009/0004055 A1* | 1/2009 | Darrigrand | A61B 10/0045 422/400 |
| 2010/0197516 A1* | 8/2010 | Holmes | G01N 33/52 506/9 |
| 2011/0117664 A1* | 5/2011 | Amisar | G01N 31/22 436/164 |
| 2011/0151570 A1 | 6/2011 | Babichenko et al. | |
| 2011/0159596 A1* | 6/2011 | Keinan | G01N 1/2211 436/52 |
| 2011/0239745 A1* | 10/2011 | Satcher, Jr. | G01N 30/90 73/61.55 |
| 2012/0295362 A1 | 11/2012 | Bland | |
| 2013/0006068 A1* | 1/2013 | Gemer | A61B 10/0051 600/314 |
| 2013/0040289 A1* | 2/2013 | Jumonville | C12Q 1/28 435/5 |
| 2013/0157381 A1* | 6/2013 | Pang | G01N 33/5302 436/501 |
| 2014/0017802 A1* | 1/2014 | Smith | G01N 21/78 436/164 |
| 2014/0134073 A1* | 5/2014 | Fuller | G01N 1/18 422/411 |
| 2015/0017732 A1 | 1/2015 | Wu et al. | |
| 2015/0185125 A1* | 7/2015 | Danylewych-May | G01N 1/02 436/174 |
| 2015/0268215 A1* | 9/2015 | Tomellini | G01N 33/227 436/93 |
| 2016/0018424 A1* | 1/2016 | Lucas | G01N 33/52 436/93 |
| 2016/0077013 A1* | 3/2016 | Attar | G01N 31/22 422/402 |
| 2016/0109371 A1* | 4/2016 | Blair | G01N 21/645 436/172 |
| 2017/0082550 A1* | 3/2017 | Callahan | G01N 21/78 |

OTHER PUBLICATIONS

World drug report 2014: Opiates; https://www.unodc.org/wdr2014/en/opiates.html.

World drug report 2014: Cocaine; https://www.unodc.org/wdr2014/en/cocaine.html.

United Nations Office on Drugs and Crime, Laboratory and Scientific Section United Nations Office on Drugs and Crime, Vienna: Recommended methods for the Identification and analysis of amphetamine, methamphetamine and their ring-substituted analogues in seized materials. Revised and updated. Manual for use by national drug testing laboratories. United nations—New York, 2006.

Zakrzewska, A., et al. Visualization of amphetamine and its analogues in TLC. Acta Chim. Slov. 2007, 54, 106-109.

Recommended methods for testing opium, morphine and heroin. https://www.unodc.org/pdf/publications/st-nar-29-rev1.pdf, 1998.

* cited by examiner

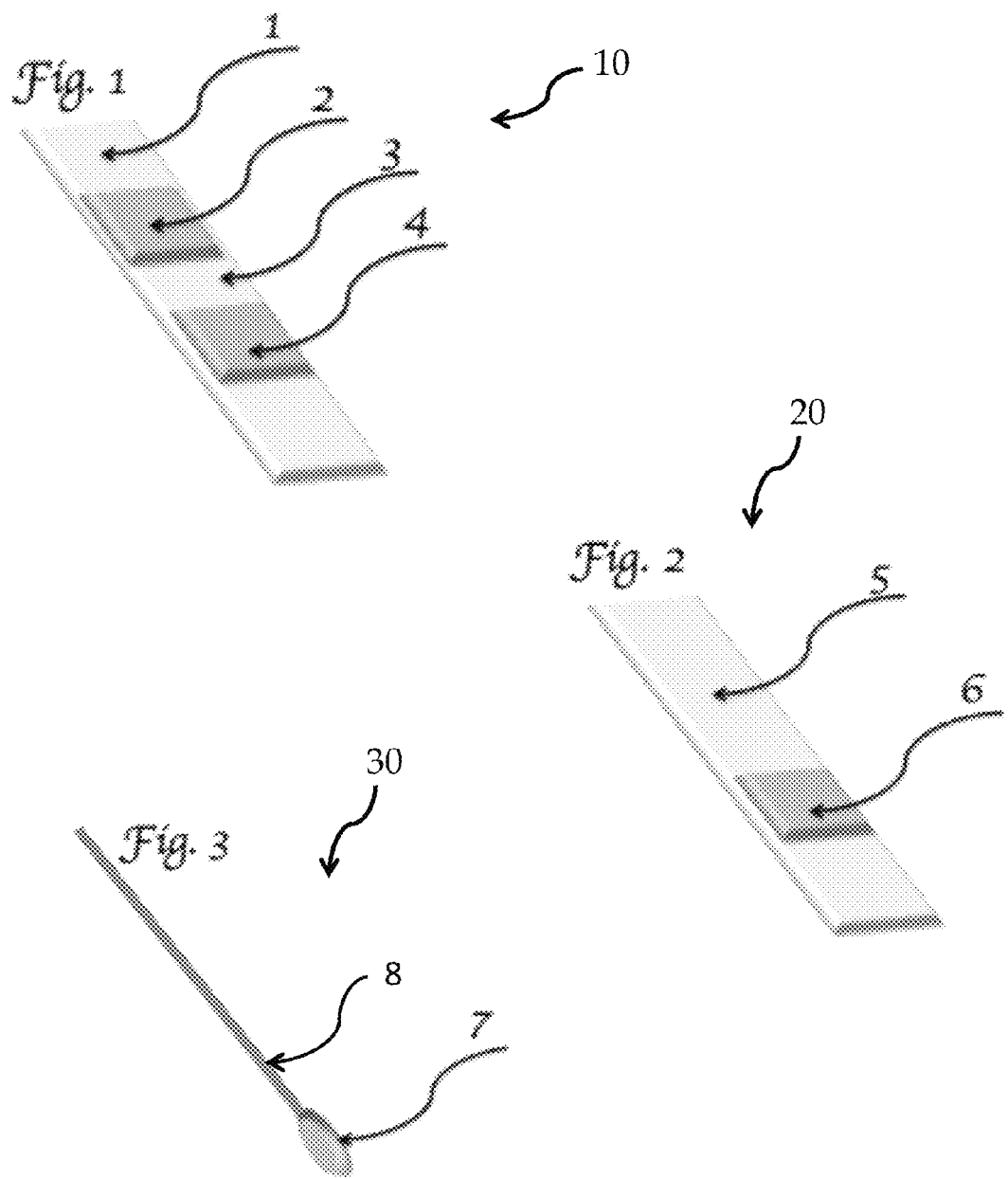

MASS PRODUCED, LOW COST, PORTABLE TEST KIT FOR THE DETECTION AND IDENTIFICATION OF NARCOTICS

RELATED APPLICATION DATA

The present application is related to commonly-owned and co-pending U.S. application Ser. No. 14/856,671, entitled PORTABLE LIQUID ANALYZER, filed on Sep. 17, 2015, which application is incorporated herein by reference in its entirety.

TECHNICAL FIELD OF THE INVENTION

The present invention relates to a portable test kit capable of identifying the presence of Amphetamine, Cannabis, Cocaine, Heroin, selected synthetic Cannabinoid and amphetamine based Cathinone type stimulants, and cannabis consumable products, a process to inexpensively mass produce the portable test kit and achieve long term commercial shelf life in the range of 2 to 3 years, and a method to use the portable test kit.

BACKGROUND ART

The global presence of drugs of abuse continues to expand. In 2014, approximately 144 tons of amphetamine class narcotics were seized globally. Cannabis plant material in 2012 was estimated at 5,350 tons, with an additional 1,269 tons of Cannabis resin seized.[1] Opiates type stimulants account for most drug related disease and deaths worldwide. Globally, most regions have seen increased opium poppy cultivation. An emerging phenomenon among opioid-dependent drug users in the United States of America is that synthetic opioids are being replaced with heroin.[2] Seizures of Cocanie have increased from 634 tons to 671 tons between 2011 and 2012. The most problematic use of cocaine is in the Americas, with an increase in prevalence recently observed in the United States.[3] North America accounted for half of all of these seizures, with the remainder spread throughout the world.[1] New regulations in the United States, specifically Colorado and Washington, allow legal Cannabis production, supply and recreational use. It remains to be seen what impact these regulatory changes will have and adding to the uncertainty is an influx in the number of synthetic un-regulated narcotics and novelties such as edible cannabis candies.[2] Globally, drugs of abuse remain an ever present threat in all sectors of society. Clearly, there is a ready need for low cost, mass producible, test kits for rapid identification of said drugs of abuse.

Most commercially available presumptive narcotic test devices and available IP and literature, use and describe methods which contain hazardous materials and sophisticated packaging which are not suitable for extremely cheap mass production in simple factory settings.

By way of example, prior art commercially available presumptive narcotic test kits include: NIK® Presumptive Drug Tests, ODV™ Narcopouch® Presumptive Drug Tests, Field Forensics DABIT® Presumptive Drugs Tests, DanceSafe Test Kits, EzTest Australia, D4D (MD-1) and C&H (MD-2), Mistral PDT and Aerosol Drug Tests.

These narcotic test kits suffer from a variety of manufacture and end use problems, including but not limited to: (i) kit construction requires liquid dropper bottles, breakable glass or plastic ampoules, blister packs and pressurized aerosol spray cans filled with hazardous liquid reagents; (ii) the presence of hazardous liquid reagents poses problems with manufacturing and exposure limitations, storage and handling, strict packaging requirements and significant shipping restrictions; (iii) the volume or quantity of liquid reagent consumed during one single test is excessive and wasteful adding to costly, bulky and often overly complicated device construction design and packaging; (iv) during use, operators may be exposed to sharps and hazardous liquid reagent splash or overspray; (v) most prior art devices require multi-step operations in order to complete a single test; and (vi) none of the prior art kits and devices achieve the bench mark of true low cost mass manufacturing, which would be considered in the range of tens of millions of individual units per annum, with a commercial shelf life span of 2 to 3 years.

As pointed out, there are many methods of presenting kits for presumptive identification of Amphetamine, Cannabis, Cocaine, Heroin, as well as intellectual property and public domain literature. Most however do not also claim detection and identification of selected synthetic Cannabinoid and amphetamine based Cathinone type stimulants and cannabis consumable products. Without limitation and by way of example only, a relevant selection of this literature is presented.

United Nations Office on Drugs and Crime publication(s) [4] and Zakrzewska, A., et al. [5] describe the use of diazonium salts (e.g. Fast Black K salt) dissolved in organic solvents for visualization of Amphetamine type stimulants when sprayed onto developed TLC plates.

U.S. Pat. No. 8,124,420 discloses a method for broad drugs of abuse screening and identification utilizing two separate colorimetric test devices. The first device utilizes diazonium salts (e.g. Fast Corinth V and Fast Black K salts) for the identification of Amphetamine and Cannabis type stimulants. The diazonium salts are prepared by sophisticated laboratory procedures and then packaged in breakable ampoules in combination with additional sealed ampoules of organic solvents (e.g. Methylene chloride or DMSO). A suspect residue obtained with an additional sophisticated multi-layer swab paper is added to the two ampoules in a container of sorts, the ampoules must be broken and all ingredients mixed together to produce a color indication. Many problems exist with this particular system: the methylene chloride is a hazardous and flammable organic solvent; DMSO, if used and presented alone as disclosed, will, in most working environments freeze and prevent the kit from functioning; the diazonium salt powder as disclosed requires sophisticated laboratory equipment and reagents for preparation and very sophisticated temperature and ambient gas-controlled ampoule sealing equipment to prevent contamination during diazonium powder packaging; the quantity of diazonium salt and organic solvent required for one single test is very costly and wasteful; the overall disclosure is not suitable for low cost, single unit, mass production.

U.S. Pat. No. 3,713,779, U.S. Pat. No. 3,748,098 and U.S. Pat. No. 7,384,599, disclose colorimetric test kits which consist of breakable ampoules filled with hazardous liquid reagents. U.S. Pat. App. No. 20150017732 discloses a similar test kit for the detection of Amphetamines, Opiates, synthetic Cannabinoids and Cathinones, wherein the kit consists of ampoules filled with known hazardous liquid reagents including, but not limited to, Dragendorf, Simons, Scott's and Marquis reagents. Additional ampoules are filled with solutions of methyl orange, xylenol orange, calmagite, FD&C blue 1, metanil yellow, 1-(2-hydroxyl-1-naphthylazo)-2-naphthol-4-sulfonic acid zinc salt, 3-((E)-(4-((E)-(4-amino-7-sulfonatonaphthalen-1-yl)diazenyl)-7-sulfonatonaphthalen-1-yl)diazenyl)naphthalene-1,5-disulfonate sodium salt, 2-((4-hydroxyphenyl)(4-oxocyclohexa-2,5-dien-1-ylidene)methyl)benzenesulfonate sodium salt, or 4-((E)-(4-(ethylamino)-3-methylphenyl)((E)-4-(ethylimino) cyclohexa-2,5-dien-1-ylidene)methyl)-3-sulfobenzenesulfonate sodium salt.

A further example of alternative packaging methods to provide a useable colorimetric test kit is disclosed in U.S. Pat. No. 4,965,047 and U.S. Pat. No. 4,196,167 which describe blister pack devices filled with solutions of hazardous reagents which change color in the presence of Cannabis type stimulants. Blister packaging requires both sophisticated industrial equipment for dispensing aliquots of liquid reagents into, and sealing blisters or pressure sensitive adhesive closure films. The quantity of reagent used per blister test is excessive. This device construction is also not suitable for mass manufacture of low cost individual test kits.

Yet another method for packaging sensitive reagents to increase shelf life is disclosed in U.S. Pat. No. 4,771,005 which describes a device for Marijuana detection consisting of pressurized spray cans filled with diazonium salt solutions including: Fast Blue B salt, Fast Garnet, Fast Red, Fast Corinth V, Fast Blue BB.

U.S. Pat. No. 7,374,946 and U.S. Pat. App. No. 20050130312 disclose a method for the presumptive identification of Amphetamine type stimulants based on time of color development when reacted with mineral acids of varying concentration and applied heat. The disclosed method requires hazardous and corrosive liquids and heating equipment, in a laboratory setting.

U.S. Pat. No. 4,288,344 discloses a method for improving the shelf life of a diazonium salt by instantaneous generation of said diazonium salt with precursor reagents dissolved in methyl cellosolve, which can react in the presence of Cannabinoids to produce a characteristic colored product. Here again, the disclosed method requires highly toxic solvents and solutions and bulky sophisticated packaging and reaction vessels.

Many bibulous carrier kits, pre-impregnated with Amphetamine and Cannabis type stimulant color change reagents are known. U.S. Pat. No. 5,523,051, U.S. Pat. No. 4,752,448 and WO1984002397A1 disclose bibulous carriers impregnated with Dragendorf and Chloroplatinic acid reagents. Although the Dragendorf reagent is capable of being dried into a bibulous carrier, the disclosure has not explained how to overcome the presence of concentrated hydrochloric acid in a standard Dragendorf reagent mixture. Without replacing this reagent with a suitable alternative, removal of concentrated acid fume is very complicated. False positive indications are frequent with these presumptive reagents due to the broad spectrum nature of color detection which reduces the suitability of this kit type for use in law enforcement. U.S. Pat. App. No. 20120295362 discloses a Marquis reagent impregnated paper strip, with a foil protective layer. In its disclosed form, this kit is unlikely to function well, as the concentrated sulphuric acid, will likely char and destroy most bibulous carrier materials within minutes and rapidly dissolve the foil protective layer. Any remaining unreacted formaldehyde would most likely evaporate. World Pat. No. 1989009395 A1 discloses a bibulous carrier strip impregnated with a diazonium salt in combination with zinc chloride. In its disclosed form, this kit is unlikely to achieve suitable commercial shelf life requirements of 2-3 years, as the diazonium salt, being extremely sensitive to ambient oxidation, hydrolysis and UV degradation will be rendered un-viable in a matter of days. The hygroscopic properties of the zinc chloride would likely increase ambient moisture content within the bibulous carrier, catalyzing breakdown of the diazonium salt. U.S. Pat. No. 3,915,639 discloses bibulous carrier strips into which ion exchange resin powders, loaded with Dragendorf, Ninhydrin and Sodium sulphate color change reagents, with the addition of color intensifying hydrazine reagent(s), are absorbed. The strips are for biological fluid analysis. As an example, this disclosure describes a weakly alkaline amine-type ion-exchange resin which is to be loaded with an acidic solution of Dragendorf reagent. The difference in pH of both components is not complimentary and post drying to a powdered product, would jeopardize the long term viability. It is likely that this mixture would remain wet, complicating subsequent manufacturing steps. Also described is the addition of color intensifying hydrazine reagents, for example di-nitro-phenyl hydrazine which is a hazardous, shock and friction explosive, not ideal for storage, shipping, packaging and handling. Further, the presence of the amine groups, both in the exchange resin and color intensifying agent, are likely to react with the Dragendorf reagent, providing false positive indications. U.S. Pat. No. 4,816,415 and U.S. Pat. No. 4,806,487 disclose a method to pre-concentrate marijuana from biological fluids into suitable papers and then visualize the papers with diazonium salt solutions including: Fast Blue BB salt, Fast Green salt, and Fast Bourdeaux Gp.

United Nations Office on Drugs and Crime publication [6] describes the use of liquid solution of Ferric sulphate (5 g dissolved in 100 mL water) for presumptive identification of Opium, Codeine, Morphine and Heroin type stimulants. A small sample of suspect residue is placed onto white test plate, dissolved, with mixing in few drops of water and then a few drop of the Ferric sulphate solution added, with mixing, to produce a typical dark brown/purple indication. Also described is the use of Mecke, Marquis and Nitric acid liquid reagents, with identical procedure.

United Nations Office on Drugs and Crime publication [3] describes the use of Marquis, Frohde and Mecke reagent solutions for presumptive identification of Opium, Morphine and Heroin type stimulants. The procedure is very much designed for laboratory settings and requires equipment, sample preparation and workup prior to addition of the colorimetric reagents and presumptive identification.

U.S. Pat. No. 3,955,926 discloses a method for broad drugs of abuse screening and identification. Opium is identified by preparing a bibulous carrier with dry impregnated Ferric ammonium sulphate, dissolving suspect residue in acetic acid, utilizing bench mounted equipment, then immersing the dry impregnated carrier into the acid solution facilitating a presumptive color indication. In the disclosed format it is not apparent how the dry carrier, impregnated with a hygroscopic ferric salt, will remain dry and functional for long period of time. In the disclosure, both Morphine and Heroin detection requires Ferric chloride salt and acidified solutions of Iodic acid. Both these reagents simply cannot be utilized in dry solid support carrier format, as in the current invention. These salts are far too sensitive, rendered inactive within hours, once exposed to ambient conditions.

U.S. Pat. No. 4,110,078 discloses a method for a highly specific colorimetric method for detecting the presence of opium and heroin in a sample, which comprises sample collection, dissolution in liquid halogenated hydrocarbon, shaking this organic phase with aqueous chloroplatinic acid in aqueous solution and subsequent addition of aqueous cobaltous thiocyanate in aqueous solution, followed by the development of a presumptive color indication in said organic phase. Again, this disclosure requires a laboratory setting, excessive equipment and time and is not applicable to mass production of a portable test kit. The disclosure states a highly specific test for both Opium and heroin. However, Chloroplatinic acid is a broad spectrum alkaloid detection reagent capable of detecting over the counter prescription amine products and Cobalt thiocyanate will produce positive indications with alkaloids and cocaine products, so it is highly unlikely to be specific and minimize false positive presumptive indications.

Another example, U.S. Pat. No. 5,457,054 discloses a broad spectrum detection method for illicit drugs including Heroin, consisting of preparation of stock solutions of Cobalt thiocyanate, Ammonium metavandate and yellow food coloring in methanol, immersing a woven pad into the said solution and hermetically sealing said impregnated pad inside ethylene-acrylic acid copolymer/aluminum foil/polyethylene/paper sachets ready for use. Presumptive identification of Heroin is indicated by development of a green hue.

U.S. Pat. App. No. 20110151570 discloses the use of Spectral Fluorescence Signature technology of residues in acidic solutions for the differentiation of Morphine from Heroin.

U.S. Pat. No. 3,972,992 discloses a method for the presumptive identification of Opium alkaloids utilizing amino lower alkyl ethers of the phenolic hydroxyl groups of opium alkaloids, which are linked via a peptide linkage to carboxylated latex polymers, forming reagents useful for detection of opium alkaloids in body fluids.

U.S. Pat. No. 4,840,912 discloses a method for presumptive Heroin identification which utilizes adsorbent pads impregnated with solutions of Picric acid and Anthracene. The wet impregnated pad must be packaged in highly specialized inert backing material and then a specialized glue applied around the edge of the backing and a hydrophobic blocking layer cover applied to form a type of sachet. The disclosed methodology utilizes hazardous, explosive reagents, and specialized packaging materials and equipment, none of which allows extremely cheap, mass production possible.

Deakin, A., [7] investigated various liquid acid reagents, including hydrochloric, sulfuric, nitric, and acetic acids to both enhance detection and reduce false results when using a modified Cobalt thiocyanate spot test for the detection of Cocaine free base. Said documented procedure requires a laboratory setting and equipment, reagent preparation and multiple steps to complete a single test.

Similarly, U.S. Pat. No. 3,955,926 discloses a method for broad drugs of abuse screening and identification, including Cocaine, which is detected by dissolving suspect residue in dilute acid acetic acid containing a Cobalt(II) chloride and then applying a small aliquot of said solution to an absorbent support impregnated with ammonium thiocyanate. In its disclosed format, Part A of said device requires liquid reagents and Part B comprising extremely hygroscopic ammonium thiocyanate impregnated into a solid bibulous carrier which will remain wet. The moisture content of said bibulous carrier would effectively prevent efficient kit manufacture and packaging and reduce kit reactivity with time.

U.S. Pat. No. 4,320,086 discloses a method for detection of Cocaine type stimulants which utilizes a bibulous carrier impregnated with an aqueous solution of Cobalt thiocyanate and Phosphotungstic acid dissolved in 50 ml water; then 50 ml anhydrous methanol are therein mixed. Impregnated sheets are air dried and cut to suitable size. Detection is achieved by applying a few milligrams of suspect residue to end of wetted finger and rubbing onto impregnated carrier. The disclosed method of device manufacture is very labor intensive and time consuming.

In another example, U.S. Pat. No. 4,812,413 discloses an aerosolized spray reagent kit for the detection of Cocaine type stimulants, based on a modified Scott's reagent. The modified reagent consists of an aqueous solution of Cobalt thiocyanate, combinations of polyols including glycerine and propyleneglycol, and various emulsifying, antifoam and inert pressurized gases. The disclosed device is a specialized and costly manufacturing process. The packaging is costly and adds greatly to downstream rubbish disposal. Users are exposed to aerosolized reagent particles and spray drift.

In a further example of a modified Scott's reagent, U.S. Pat. No. 5,753,513 discloses a reagent solutions consisting of Cobalt thiocyanate, a polyol chosen from a group consisting of propylene glycol, 1,3-propane-diol, 1,4-butanediol, ethylene glycol, poly-ethylene glycol (PEG) 200, PEG-400, PEG-600, diethylene glycol mono ethyl-ether, polypropylene glycol (PPG) 200, PPG-400, and PPG-600 and an acid solution chosen from acetic, hydrochloric, citric and, or phosphoric acids. The reagent solutions are provided in bottle containers.

In yet another example of a modified Scott's test, U.S. Pat. No. 6,133,040 discloses a method of introducing an additional reaction step for presumptive identification of Cocaine type stimulants involving reaction with an organic solvent solution of pH phthalein indicator. Here again the test kit consists of many bottles of various hazardous liquid reagents and is more suited to a laboratory setting.

Impregnation of bibulous carriers with reagent solutions is an incredibly inefficient and costly method of presumptive test kit manufacture. Ultimately, the solvents used to dissolve the powdered reagents must be removed by evaporation. Often the solvents will be aqueous based and acidic in nature, which makes removal from the bibulous carrier hazardous, very costly, and will require very sophisticated laboratory equipment to minimize exposure and corrosion of the surrounds. In the event that the bibulous carrier can be dried, it must still be cut and presented in a kit format for ease of use. Often, this will incorporate plastic injection molded housings, which are magnitudes of order more expensive than paper based supports. Additionally, the cost of the injection die is excessive. The alternative low cost paper based solid support carrier option for a presumptive kit is often not possible, as the loaded bibulous carrier strips resist sticking and adhering to common pressure sensitive adhesives because of interaction with the impregnated reagent(s) and/or the pressure sensitive adhesives react with the impregnated reagent(s), destroying the kits.

SUMMARY OF THE INVENTION

Embodiments of the present invention provide a presumptive spot test kit which will facilitate identification of Amphetamine, Cannabis, Cocaine, Heroin, selected synthetic Cannabinoid and amphetamine based Cathinone type stimulants and cannabis consumable products within suspect residues, be they liquid or solid.

Embodiments of the present invention provide a presumptive kit, constructed of paper with color change reagents applied to the surface as one or more test zones, and a pre-wetted swab with non-hazardous co-solvents to facilitate enhanced suspect residue collection.

Embodiments of the present invention provide an extremely portable presumptive test kit, which has true low cost and mass manufacture capability on the order of millions of units per annum, while achieving a commercial kit shelf life, on the order of several years, with a reduced false detection rate.

Embodiments of the present invention also provide a method of kit manufacture and use.

BRIEF DESCRIPTION OF THE DRAWINGS

FIG. 1 illustrates an embodiment of a diagnostic test paper made in accordance with the present invention;

FIG. 2 illustrates another embodiment of a diagnostic test paper made in accordance with the present invention;

FIG. 3 illustrates an embodiment of a swab made in accordance with the present invention.

DETAILED DESCRIPTION OF THE PREFERRED EMBODIMENT

Figure 4:
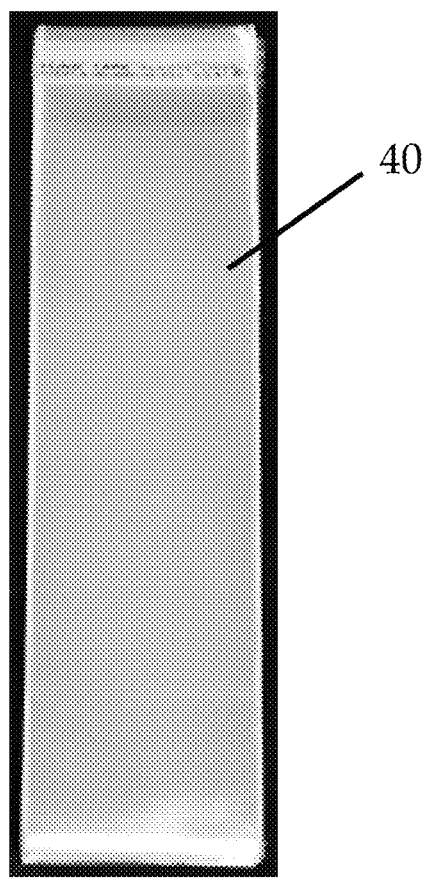
FIG. 4 illustrates a package into which a test paper and swab may be hermetically sealed.

The described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention can be practiced without one or more of the specific details, or with other methods, components and so forth. In other instances, well-known structures, materials, or operations are not shown or described in detail to avoid obscuring aspects of the invention.

Contrary to the prior approaches for the presumptive identification of Amphetamine, Cannabis, Cocaine, Heroin, selected synthetic Cannabinoid and amphetamine based Cathinone type stimulants, and cannabis consumable products, the inventor has discovered that presumptive polyvalent ion powdered salts, carbohydrates and polyols and color change reagents can be successfully mixed with and/or made into encapsulating polymer solutions and printed onto any solid support structure, to be shaped and packaged. In combination with a simple cotton swab, such as a Q-tip® swab, which has been pre-wetted with a non-hazardous solvent and packaged, Embodiments of the present invention provide a low cost, mass producible, portable test kit for the presumptive identification of Amphetamine, Cannabis, Cocaine, Heroin, selected synthetic Cannabinoid and amphetamine based Cathinone type stimulants, and cannabis consumable products.

FIG. 1 illustrates an embodiment of a diagnostic test paper 10 made in accordance with this invention. The test paper 10 comprises a solid support surface or article 1; an encapsulated alkaline salt 2, printed at one or more locations onto the support surface 1; a physical gap or void 3 between the individual encapsulated reagent deposition interstices 2 on the solid support surface 1 to prevent chemical interaction; and an encapsulated color change dye 4 printed onto the support surface 1.

FIG. 2 illustrates another embodiment of a diagnostic test paper 20 made in accordance with this invention. The test paper 20 comprises a solid support surface or article 5 and an encapsulated color change dye or polyvalent ion 6 printed onto the support surface 5.

FIG. 3 illustrates an embodiment of a swab 30, such as a Q-tips swab, made in accordance with the present invention. The swab 30 comprises a cotton tip matrix 7, pre-wetted with one or more non-hazardous solvents, attached to one end of a handle 8.

Solid Support

Suitable solid support surfaces or substrates to which the encapsulated presumptive reagents can be applied, is dictated only by end use requirements. In accordance with the current invention and without limitation, in some embodiments the solid support substrate 1, 5 is paper, such as 100-400 gsm white, acid free, card sheet.

Sample Swab

In order to maximize solubility of both the suspect residue narcotic (i.e. Amphetamine, Cannabis, Cocaine, Heroin, selected synthetic Cannabinoid and amphetamine based Cathinone type stimulants, and cannabis consumable products.) and the presumptive test reagents, a suitable non-hazardous solvent and/or solvent mix provided in combination with a swabbing device. Numerous swab and co-solvent devices can be prepared including, but not limited to, a pre-wetted cotton swab and/or co-solvent shaft filled pop or snap swabs.

In one embodiment, the sample swab 30 is a pre-wetted, co-solvent, cotton swab. Pre-wetting is achieved by simple dip and/or rapid immersion of the swab cotton tip matrix into large volume pre-mixed co-solvent vat, micro-jet spray, or the like. Pre-wetting is preferably a fully automated process utilizing conventional conveyor, hopper, spray machinery.

In an embodiment of a kit 10 to be used to test for Amphetamine, Cannabis, selected synthetic Cannabinoid and amphetamine based Cathinone type stimulants, and cannabis consumable products dissolution, the cotton swab tip 7 is pre-wetted with co-solvent mix of dimethyl sulphoxide (DMSO) and isopropyl alcohol (IPA). This co-solvent mix offers broad spectrum solubility of target narcotic and dry reagent compounds, while intensifying presumptive color change reactions. The combination of IPA with DMSO prevents freezing of solvents during long term storage and use in low temperature environments. This solvent offers broad spectrum solubility of said target narcotic and dry reagent compounds, while intensifying presumptive color change reactions. This solvent combination is non-hazardous and extremely low cost.

In an embodiment of a kit 10 to be used to test for Heroin and Cocaine type stimulants dissolution, the cotton swab tip 7 is pre-wetted with water. This solvent offers broad spectrum solubility of the target narcotics and dry reagent compounds, while intensifying presumptive color change reactions. This solvent combination is also non-hazardous and extremely low cost.

Alkaline Salt

An alkaline salt intensifies the color development between Amphetamine, Cannabis, selected synthetic Cannabinoid and amphetamine based Cathinone type stimulants, and cannabis consumable products and the color change reagents. Many suitable alkaline salts exist, including but not limited to, organic and in-organic alkaline salts.

In accordance with the current invention and without limitation, in one embodiment, the alkaline salt 2 used to catalyze is sodium hydrogen carbonate. The sodium hydrogen carbonate powder may be milled to a 1-30 micron mesh size and mixed with a standard overprint varnish encapsulation emulsion. The resulting homogenized suspension is adjusted to the correct viscosity for laydown, printing application onto the solid support 1.

Presumptive Colorimetric Reagent—Amphetamine and Cannabis

The presumptive colorimetric reagent 4 produces a known visual color indication in the presence of Amphetamine, Cannabis and some synthetic Cannabinoid and amphetamine based Cathinone type stimulants, thus identifying these classes of compounds within unknown suspect residues, be they solid or liquid. Numerous color change dyes exist, including but not limited to: 2,5-Dimethoxy-4-([4- nitrophenyl]azo)benzenediazonium chloride hemi(zinc chloride) salt, 2-Methoxy-5-methyl-4-[(4-methyl-2-nitrophenyl)azo]benzenediazonium tetrachlorozincate, 2-Methoxy-4-nitrobenzenediazonium chloride hemi(zinc chloride) salt, 3,3'-dimethoxy[1,1'-biphenyl]-4,4'-bis(diazonium) dichloride, 4-benzamido-2,5-diethoxybenzene-diazonium salt zinc chloride, 4-m-Tolylazo-m-toluidine, disodium; 2-[[4-[ethyl-[(3-sulfonatophenyl)methyl]amino]phenyl]-[4-[ethyl-[(3-sulfonatophenyl)methyl]azaniumylidene]cyclohexa-2,5-dien-1-ylidene]methyl]benzenesulfonate, sodium; 4-[(2E)-2-(2-oxonaphthalen-1-ylidene)hydrazinyl]naphthalene-1-sulfonate, 4-benzamido-2,5-dimethoxybenzenediazonium, 2-methyl-4-[(2-methylphenyl)diazenyl]aniline; hydrochloride, 4-methoxy-2-nitroaniline, (1Z)-1-[(4-methyl-2-nitrophenyl)hydrazinylidene]naphthalen-2-one, disodium; (6Z)-4-amino-3-[(4-nitrophenyl)diazenyl]-5-oxo-6-(phenylhydrazinylidene)naphthalene-2,7-disulfonate, sodium; (6Z)-4-amino-3-[[4-[4-[(2,4-diaminophenyl)diazenyl]phenyl]phenyl]diazenyl]-5-oxo-6-(phenylhydrazinylidene)naphthalene-2,7-disulfonic acid, disodium; 8-(4-methylanilino)-5-[[4-[(3-sulfonatophenyl)diazenyl]naphthalen-1-yl]diazenyl]naphthalene-1-sulfonate, VB 4-N-(4-methoxyphenyl)benzene-1,4-diamine; sulfuric acid, sodium; 4-[[4-(diethylamino)phenyl]-(4-diethylazanium-ylidenecyclohexa-2,5-dien-1-ylidene)methyl]benzene-1,3-disulfonate, 1,2,5,8-tetrahydroxyanthracene-9,10-dione, 2-[(2-chloro-4-nitrophenyl)diazenyl]-5-methoxy-4-methylaniline, 4-(4-aminophenyl)aniline, sodium; (4E)-4-[(2-hydroxynaphthalen-1-yl)hydrazinylidene]-3-oxonaphthalene-1-sulfonate, pyranthrene-8,16-dione, trisodium; 4-[(4-anilino-5-sulfonatonaphthalen-1-yl)diazenyl]-5-hydroxynaphthalene-2,7-disulfonate, disodium; (8Z)-7-oxo-8-(phenylhydrazinylidene)naphthalene-1,3-disulfonate, O-Nitroaniline, 3-Amino-4-chlorobenzotrifluoride, 3-amino-N-butyl-4-methoxybenzenesulfonamide, 1-aminoanthracene-9,10-dione, 5-Chloro-2-(4-chlorophenoxy)aniline, 2,5-dichloroaniline, 4-methyl-2-nitroaniline, 4-chloro-2-nitroaniline, 2-carbamoyl-5-methoxybenzenediazonium; chloride, 3-amino-N, N-diethyl-4-methoxybenzenesulfonamide, 5-chloro-2-methoxyaniline; hydrochloride, 2-methyl-4-nitroaniline, (1Z)-1-[[2-methyl-4-[(2-methylphenyl)diazenyl]phenyl]hydrazinylidene]naphthalen-2-one, 4-benzamido-5-chloro-2-methylbenzenediazonium; chloride, 2,5-dichloroaniline, (1Z)-1-[(4-methyl-2-nitrophenyl)hydrazinylidene]naphthalen-2-one, sodium; 4-hydroxy-3-[(2E)-2-(2-oxonaphthalen-1-ylidene)hydrazinyl]benzenesulfonate, 2-chloroaniline, 4-diazo-2-chlorobenzene, 4-diazo-diphenylamine, diazotised N,N-diethyl-3-toluidine, diazotised 2-chloro-N, N-diethylaniline.

One presumptive colorimetric dye 4 that may be used for the presumptive identification of Amphetamine, Cannabis and some synthetic Cannabinoid and amphetamine based Cathinone type stimulants is a diazonium salt. In one embodiment, 2,5-Dimethoxy-4-([4-nitrophenyl]azo)benzenediazonium chloride hemi(zinc chloride) salt is mixed with a standard overprint varnish encapsulation emulsion. The homogenized suspension is adjusted to the correct viscosity for laydown, printing application, onto the solid support 1.

Presumptive Colorimetric Reagent—Heroin

The presumptive colorimetric reagent 6 produces a known visual color indication in the presence of Heroin type stimulants, thus identifying these classes of compounds within unknown suspect residues, be they solid or liquid. Numerous presumptive reagents exist, including but not limited to, combinations of polyvalent cations and anions: thiocyanates, vanadates, molybdates, sulphates, citrates, tartrates, carbonates and nitrates, cerium, lead, palladium, bismuth, tin, iron, cobalt, nickel, copper, aluminum, manganese, magnesium, and ammonium. In one embodiment, the colorimetric dye 6 for the presumptive identification of Heroin type stimulants may be a Ferric salt. The Ferric sulphate salt may be mixed with a standard overprint varnish encapsulation emulsion. The homogenized suspension is adjusted to the correct viscosity for laydown, printing application, onto the solid support 5.

Presumptive Colorimetric Reagent—Cocaine

Another presumptive colorimetric reagent 6 produces a known visual color indication in the presence of Cocaine type stimulants, thus identifying this class of compounds within unknown suspect residues, be they solid or liquid. Numerous presumptive reagents exist, including but not limited to, combinations of polyvalent cations and anions: thiocyanates, vanadates, molybdates, sulphates, citrates, tartrates, carbonates and nitrates, cerium, lead, palladium, bismuth, tin, iron, cobalt, nickel, copper, aluminum, manganese, magnesium, and ammonium. In one embodiment, the presumptive colorimetric dye 6 for the presumptive identification of Cocaine type stimulants is a Cobalt salt. The Cobalt thiocyanate salt may be mixed with a polyol and a carbohydrate and an acid to form an encapsulation emulsion. The emulsion is adjusted to the correct viscosity for laydown, printing application, onto the solid support 5.

Encapsulation Emulsion

The encapsulation polymer emulsion remains inert to all presumptive reagents during mixing, laydown printing, and long term storage of the finished product. The use of the encapsulation emulsion is an extremely simple, uncomplicated method of encapsulating highly sensitive reagents and providing a workable material for solid support surface deposition. Once dried, the encapsulating polymer protects the reagents from ambient moisture, air, and abrasion. In one embodiment, the encapsulation polymer used for producing kits for detection of Amphetamine, Cannabis and Heroin type stimulants may be chosen from Joncryl, Fujifilm, Sericol, Carboset, Krumbhaar, and Marabu standard overprint varnish products.

In another embodiment, the encapsulation polymer used for producing kits for detection of Cocaine type stimulants may consist of a polyol, a carbohydrate, and an acid. An advantage of this encapsulation emulsion system is the provision of the necessary functional organic character, alcohol function group, and acidity to facilitate a modified Scott's Cocaine type detection of both Cocaine Hydrochloride and Cocaine free base. Additionally, the emulsion carbohydrate provides an important tertiary function of maintaining a dry hardened encapsulated reagent matrix post laydown printing and drying. This improves long term storage for several years.

In one embodiment, the encapsulation emulsion may consist of glycerol, sucrose, mannitol, or sodium hydrogen sulphate.

Reagent and Encapsulating Polymer Mixing

In embodiments of the present invention, all dry powder presumptive reagents are individually micronized in suitable a agitation mill system such as a laboratory ball, crusher, shaker mill, or the like. In correct reagent to encapsulating polymer/emulsion ratios, all micronized powders and encapsulating liquid polymers are mixed in inert mixing containers using high speed agitation or shaker beds or rotary impeller mixers to produce homogenized flowable emulsions capable of undergoing laydown print applications.

Reagent Deposition

Deposition of the powdered reagent(s) and encapsulation emulsion mixture can be achieved by any suitable large scale printing system using standard factory equipment. For example, letterpress, rotary gravure, screen printing, tampography, wax printing, contact dosing, ultrasonic sputter, and spray and drop on demand printing may be used.

In one embodiment, the encapsulation and presumptive reagent mixture(s) may be printed, together or individually, onto a 100-400 gsm card using any suitable screen printing process and dried. Preferably the screen-printing machinery is fully automated. Any of a number of drying processes may be used, such as of forced-air, UV, IR, and hot air cure.

In another embodiment illustrated in FIG. 1, the individual dried encapsulated chemical reagents 2 may be printed onto the solid support article 1 separated by a physical space 3 between the individual encapsulated reagent deposition interstices 2, thus preventing chemical interaction and contamination of the reagents 2 and maintain selectivity and reactivity for target molecule(s) and ion(s).

Device Shaping

Large individual or continuous printed roll sheets to be used for the support surface 1, 5 may be shaped into any form and any dimension for final device presentation. In one embodiment the support surface 1, 5 is a small hand held paper strip, which is extremely simple to produce through automated die cutting and guillotining systems.

Packaging

In one embodiment of the present invention, the test kit, comprising both the sample collection swab 30 and a printed dry reagent presumptive test strip 10 or 20, may be packaged individually in separate, moisture and UV resistant packages 40 (FIG. 4) prior to use. Preferably the package 40 is a tear-open, form, fill, and seal sachet. The sachet 40 may be constructed from commercially available Paper/PET12 um/AL7 um/PE50 product, which is an extremely cheap, mass produced material. Individual pre-wetted sample swabs 30 and individual printed dry reagent presumptive test strips 10, 20 may be automatically packaged into individual sachets 40 by vertical and/or horizontal form/seal machines.

Use of Kit

The kit (test strip 10, 20, swab 30, in the sealed package 40) may be carried in a pocket, belt case, glove box, brief case, etc. When a suspect residue or object is observed, both the sampling swab 30 and presumptive reagent strip 10, 20 are removed from the sachet packaging 40. The swab 30 is rubbed into the suspect residue, liquid, gel, solid and/or across suitable surfaces for several seconds, to facilitate the collection of a representative sample of the suspect residue. The swab 30 with the collected sample is then rubbed through both the encapsulated alkaline salt 2 and encapsulated presumptive reagent dye 4 test zones on the paper strip for several seconds, facilitating a rapid yes/no positive/negative colorimetric indication for the presence Amphetamine, Cannabis and some synthetic Cannabinoid and amphetamine based Cathinone type stimulants.

Color Indications

In accordance with embodiments of the current invention and without limitation, example results are provided: (Control swab—Negative) no color indication; (Methamphetaime—ice/speed—Positive) instant red indication; (MDMA—ecstacy—Positive) instant red indication; (Cannabis plant—Positive) instant purple indication; (Mephidrone—Positive) instant red indication; (Cannabichromene—Positive) instant purple indication; (Methylone—Positive) instant red indication; (Oxycodone—Negative) no color indication; (Codeine—Negative) no color indication; (Pyvalerone—Negative) no color indication; (Naphyrone—Negative) no color indication; (Stevia—Negative) no color indication; (Benzocaine—Negative) no color indication; (Lidocaine—Negative) no color indication; (Diphenhydramine—Negative) no color indication; (Guaifenesin—Negative) no color indication; (Caffeine—Negative) no color indication; (Methocarbomol—Negative) no color indication; (Heroin—Negative) no color indication; (Glucosamine—Negative) no color indication; (Salt—Negative) no color indication; (Psilocybin—Negative) no color indication.

In accordance with embodiments of the current invention and without limitation, further example results are provided: (Control swab—Negative) no color indication; (Methamphetaime—ice/speed—Negative) no indication; (MDMA—ecstacy—Negative) no indication; (Cannabis plant—Negative) no indication; (Mephidrone—Negative) no indication; (Cannabichromene—Negative) no indication; (Methylone—Negative) no indication; (Oxycodone—Negative) no color indication; (Codeine—Negative) no color indication; (Pyvalerone—Negative) no color indication; (Naphyrone—Negative) no color indication; (Stevia—Negative) no color indication; (Benzocaine—Negative) no color indication; (Lidocaine—Negative) no color indication; (Diphenhydramine—Negative) no color indication; (Guaifenesin—Negative) no color indication; (Caffeine—Negative) no color indication; (Methocarbomol—Negative) no color indication; (Heroin—Positive) rapid black color indication; (Glucosamine—Negative) no color indication; (Salt—Negative) no color indication; (Psilocybin—Negative) no color indication.

In accordance with embodiments of the current invention and without limitation, additional example results are provided: (Control swab—Negative) no color indication; (Cocaine HCl—Positive) Instant solid bright blue; (Cocaine free base—Positive) Slow forming solid bright blue; (Methamphetamine—False positive) Very slow forming solid bright blue; (Heroin—Positive) Slow forming solid bright blue; (Caffeine—Negative) no indication; (Methocarbomol—Negative) no indication; (MDMA—Negative) no color indication; (Codeine—Negative) no color indication; (Pyvalerone—Negative) no color indication; (Naphyrone—Negative) no color indication; (Stevia—Negative) no color indication; (Benzocaine—Negative) no color indication; (Lidocaine—Negative) no color indication; (Diphenhydramine—Negative) no color indication; (Guaifenesin—Negative) no color indication; (Glucosamine—Negative) no color indication; (Salt—Negative) no color indication; (Psilocybin—Negative) no color indication.

Examples (1) In accordance with embodiments of the current invention and without limitation, a presumptive kit for the detection and identification of Amphetamine, Cannabis and some synthetic Cannabinoid and amphetamine based Cathinone type stimulants is produced by pre-wetting a cotton swab 30 with 0.01 to 0.05 mL of DMSO:IPA (75:25) co-solvent and individually packaging the swab 30 into a form fill Paper/PET12 um/AL7 um/PE50 sachet 40. Continuous or individual sheet fed 300 gsm white acid free card 1 is first printed with individual strips of encapsulated micronized powder sodium bicarbonate:over print varnish:thinners emulsion (30:30:40) 2 by off-set screen printing using 32-64 mesh screen and air dried. The printed sheets are re-fed for second laydown printing of encapsulated 2,5-Dimethoxy-4-([4-nitrophenyl]azo)benzenediazonium chloride hemi(zinc chloride) salt:over print varnish:thinners emulsion (5:30:65) 4 and air dried. The print, on the large scale sheet or continuous roll, has achieved 1-3 mm gap 3 between the intercies of the bicarbonate and reagent dye test zones. The large scale printed sheets or continuous rolls are die cut into individual strips, which are subsequently individually packaged into the sachets 40 and hermetically sealed.

(2) In accordance with embodiments of the current invention and without limitation, a presumptive kit for the detection and identification of Heroin type stimulants is produced by pre-wetting a cotton swab 30 with 0.01 to 0.05 mL water and individually packaging the swab 30 into a form fill Paper/PET12 um/AL7 um/PE50 sachet 40. Continuous or individual sheet fed 300 gsm white acid free card 1 is printed with individual strips of encapsulated micronized powdered Ferric sulpahte:over print varnish:thinners emulsion (20:35:45) 2 by off-set screen printing using 32-64 mesh screen and air dried. The large scale printed sheets or continuous rolls are die cut into individual strips, which are subsequently individually packaged into the sachets 40 and hermetically sealed.

(3) In accordance with the current invention and without limitation, a presumptive kit for the detection and identification of Cocaine type stimulants is produced by pre-wetting a cotton swab 30 with 0.01 to 0.05 mL water 3 and individually packaging the swab 30 into a form fill Paper/PET12 um/AL7 um/PE50 sachet 40. Continuous or individual sheet fed 300 gsm white acid free card 1 is printed with individual strips of encapsulated micronized powdered Cobalt thiocyanate: Sucrose: Mannitol: Glycerol: Water: Sodium Hydrogen Sulphate emulsion (5:10:21:11:49:4) 2 by off-set screen printing using 32-64 mesh screen and air dried. The large scale printed sheets or continuous rolls are die cut into individual strips, which are subsequently individually packaged into the sachets 40 and hermetically sealed.

Embodiments of test kits the present invention provide numerous benefits over existing test methods. Among such benefits:

The test kits of the present invention replace the need for sample workup and preparation in a laboratory setting as required by TLC analysis and remove the hazardous liquified diazonium salt spray or other hazardous liquid reagents, with a miniature, highly portable, dry stabilized diazonium salt test strip. Sample preparation, laboratory equipment, and numerous sequential steps are not required to perform the test.

The test kits of the present invention replace all sophisticated laboratory procedures and equipment, with a single step diazonium salt encapsulation and paper strip laydown methodology. The test kits do not require breakable ampoule packaging, and prevent solvents like DMSO from freezing by the addition of non-hazardous, low cost co-solvent. Further, single test kits are designed for mass manufacture at low cost with a 2 to 3 year shelf life and have a greatly reduced false indication rate.

The description of the present invention has been presented for purposes of illustration and description, but is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A portable detection kit for identifying the presence of a target narcotic, comprising:
   a homogenous suspension of a dry chemical powder reagent mixed with an inert liquid encapsulating polymer, deposited and dried onto a solid support article, wherein the dry coated chemical powder reagent is encapsulated and thereby protected by the inert liquid polymer;
   a swab device pre-wetted with a solvent to facilitate the collection and transfer of a suspected residue to the reagent coated solid support article and upon contacting the narcotic residue with the reagent coated solid support article and mixing all components together on the solid support article, a known visual colorimetric indication is produced identifying a class of an unknown target narcotic present in the suspect residue; and
   a light, air, and moisture proof package into which the reagent coated solid support article and the swab device are individual hermetically sealed prior to use.

2. The portable detection kit as in claim 1, wherein the target narcotic is selected from the group consisting of Amphetamine, Cannabis, Cocaine, Heroin, selected synthetic Cannabinoid and amphetamine based Cathinone type stimulants, and cannabis consumable products.

3. The portable detection kit as in claim 1, wherein the chemical reagent comprises a dry micronized powder comprising an organic or inorganic salt of polyvalent ions or an organic dye salt, which undergo characteristic color change when combined with the target narcotic.

4. The portable detection kit as in claim 3, wherein the organic and inorganic salts of polyvalent ions are selected from the group consisting of cobalt thiocyanate, ammonium vanadate, molybdic acid, sodium molybdate, ammonium molybdate, copper sulphate, dimethylamino benzaldehyde, gallic acid, and vanillin, dimethylamino cinnamaldehyde for detection of an Amphetamine and Cannabis type stimulants.

5. The portable detection kit as in claim 3, wherein the organic dye salts are selected from the group consisting of diazonium, azo, triarylmethane, nitro, nitroso, fluorone, xanthene, quinone-imine, ketonamine, acridine, pyronin, phthalocyanine, anthraquinone, diarylmethane, thiazin, oxazin, safranin, eurhodin, rhodamine, thiazole, aminoketone, indigoid, natural, azin, tetrazolium, and indophenol classes of dyes for detection of an Amphetamine type stimulant.

6. The portable detection kit as in claim 3, wherein the organic dye salts are selected from the group consisting of 2,5-Dimethoxy-4-([4-nitrophenyl]azo)benzenediazonium chloride hemi(zinc chloride) salt, 2-Methoxy-5-methyl-4-[(4-methyl-2-nitrophenyl)azo]benzenediazonium tetrachlorozincate, 2-Methoxy-4-nitrobenzenediazonium chloride hemi(zinc chloride) salt, 3,3'-dimethoxy[1,1'-biphenyl]-4,4'-bis(diazonium) dichloride, 4-benzamido-2,5-diethoxybenzene-diazonium salt zinc chloride, 4-m-Tolylazo-m-toluidine, disodium; 2-[[4-[ethyl-[(3-sulfonatophenyl)methyl]amino]phenyl]-4-[ethyl-[(3-sulfonatophenyl)methyl]azaniumylidene]cyclohexa-2,5-dien-1-ylidene]methyl]benzenesulfonate, sodium; 4-[(2E)-2-(2-oxonaphthalen-1-ylidene)hydrazinyl]naphthalene-1-sulfonate, 4-benzamido-2,5-dimethoxybenzenediazonium, 2-methyl-4-[(2-methylphenyl)diazenyl]aniline; hydrochloride, 4-methoxy-2-nitroaniline, (1Z)-1-[(4-methyl-2-nitrophenyl)hydrazinylidene]naphthalen-2-one, disodium; (6Z)-4-amino-3-[(4-nitrophenyl)diazenyl]-5-oxo-6-(phenylhydrazinylidene)naphthalene-2,7-disulfonate, sodium; (6Z)-4-amino-3-[[4-[(2,4-diaminophenyl)diazenyl]phenyl]phenyl]diazenyl]-5-oxo-6-(phenylhydrazinylidene)naphthalene-2,7-disulfonic acid, disodium; 8-(4-methylanilino)-5-[[4-[(3-sulfonatophenyl)diazenyl] naphthalen-1-yl]diazenyl]naphthalene-1-sulfonate, VB 4-N-(4-methoxyphenyl)benzene-1,4-diamine; sulfuric acid, sodium; 4-[[4-(diethylamino)phenyl]-(4-diethylazanium-ylidenecyclohexa-2,5-dien-1-ylidene)methyl]benzene-1,3-disulfonate, 1,2,5,8-tetrahydroxyanthracene-9,10-dione, 2-[(2-chloro-4-nitrophenyl)diazenyl]-5-methoxy-4-methylaniline, 4-(4-aminophenyl)aniline, sodium; (4E)-4-[(2-hydroxynaphthalen-1-yl)hydrazinylidene]-3-oxonaphthalene-1-sulfonate, pyranthrene-8,16-dione, trisodium; 4-[(4-anilino-5-sulfonatonaphthalen-1-yl)diazenyl]-5-hydroxynaphthalene-2,7-disulfonate, disodium; (8Z)-7-oxo-8-(phenylhydrazinylidene)naphthalene-1,3-disulfonate, O-Nitroaniline, 3-Amino-4-chlorobenzotrifluoride, 3-amino-N-butyl-4-methoxybenzenesulfonamide, 1-aminoanthracene-9,10-dione, 5-Chloro-2-(4-chlorophenoxy)aniline, 2,5-dichloroaniline, 4-methyl-2-nitroaniline, 4-chloro-2-nitroaniline, 2-carbamoyl-5-methoxybenzenediazonium; chloride, 3-amino-N, N-diethyl-4-methoxybenzenesulfonamide, 5-chloro-2-methoxyaniline; hydrochloride, 2-methyl-4-nitroaniline, (1Z)-1-[[2-methyl-4-[(2-methylphenyl)diazenyl]phenyl]hydrazinylidene]naphthalen-2-one, 4-benzamido-5-chloro-2-methylbenzenediazonium; chloride, 2,5-dichloroaniline, (1Z)-1-[(4-methyl-2-nitrophenyl) hydrazinylidene]naphthalen-2-one, sodium; 4-hydroxy-3-[(2E)-2-(2-oxonaphthalen-1-ylidene)hydrazinyl] benzenesulfonate, 2-chloroaniline, 4-diazo-2-chlorobenzene, 4-diazo-diphenylamine, diazotised N, N-diethyl-3-toluidine, diazotised 2-chloro-N, and N-diethylaniline for detection of an Amphetamine type stimulant.

7. The portable detection kit as in claim 3, wherein the characteristic color change proceeds regardless of the presence of a catalytic dry powdered alkaline organic or inorganic salt.

8. The portable detection kit as in claim 3, wherein the liquid encapsulating polymer is selected from the group consisting of acrylic emulsions, polyvinyl alcohol, polyvinyl pyrrolidone, glycol-ethers, styrene, polyester, polybutadiene, alginate, guar, polyethylene, urea, natural gums, polyether and polyamide units, styrene acrylic copolymer emulsion, Isophthalic alkyd, Nitrocellulose, Cellulose Acetate Propionate (CAP), Vinyl chloride acetate co-polymer, Polyamide, and hexamethoxymethyl melamine resin.

9. The portable detection kit as in claim 3, wherein the organic and inorganic salts of polyvalent ions are selected from the group consisting of thiocyanates, vanadates, molybdates, sulphates, citrates, tartrates, carbonates and nitrates for detection of a Heroin type stimulant.

10. The portable detection kit as in claim 9, wherein the polyvalent ions are selected from the group consisting of Cerium, Lead, Palladium, Bismuth, Tin, Iron, Cobalt, Nickel, Copper, Aluminum, Manganese, Magnesium, and Ammonium for detection of a Heroin type stimulant.

11. The portable detection kit as in claim 9, wherein the characteristic color change proceeds regardless of the presence of a catalytic dry powdered alkaline organic or inorganic salt.

12. The portable detection kit as in claim 11, wherein the catalytic dry powdered alkaline salt is selected from the group consisting of sodium carbonate, trisodium citrate, sodium hydrogen carbonate, calcium carbonate, sodium and ammonium hydroxide.

13. The portable detection kit as in claim 9, wherein the liquid encapsulating polymer is selected from the group consisting of acrylic emulsions, polyvinyl alcohol, polyvinyl pyrrolidone, glycol-ethers, styrene, polyester, polybutadiene, alginate, guar, polyethylene, urea, natural gums, polyether and polyamide units, styrene acrylic copolymer emulsion, Isophthalic alkyd, Nitrocellulose, Cellulose Acetate Propionate (CAP), Vinyl chloride acetate co-polymer, Polyamide, and hexamethoxymethyl melamine resin.

14. The portable detection kit as in claim 3, wherein the organic and inorganic salts of polyvalent ions are selected from the group consisting of thiocyanates, vanadates, molybdates, sulphates, citrates, tartrates, carbonates and nitrates for detection of a Cocaine type stimulant.

15. The portable detection kit as in claim 14, wherein the polyvalent ion is selected from the group consisting of Cerium, Lead, Palladium, Bismuth, Tin, Iron, Cobalt, Nickel, Copper, Aluminum, Manganese, Magnesium, and Ammonium.

16. The portable detection kit as in claim 3, wherein the inert liquid encapsulating polymer is selected from the group consisting of polyols, water, carbohydrates, and acids.

17. The portable detection kit as in claim 16, wherein:
the polyols comprise glycerol;
the carbohydrates are selected from the group consisting of mannitol, sucrose, fructose, hexose, and starches; and
the acids are selected from the group consisting of sodium hydrogen sulphate, citric acid, tartaric acid, and ascorbic acid.

18. The portable detection kit as in claim 1, wherein the powdered reagent comprises a plurality of powdered reagents separated from one another throughout all kit production steps.

19. The portable detection kit as in claim 1, wherein the powdered reagent comprises a plurality of powdered reagents mixed together into an homogenous powdered reagent mix.

20. The portable detection kit as in claim 19, wherein, the mixture of the plurality of reagent powders and the inert liquid encapsulating polymer comprises a stable, low viscosity, homogenized suspension.

21. The portable detection kit as in claim 1, wherein the inert liquid encapsulating polymer comprises an aqueous liquid encapsulating polymer.

22. The portable detection kit as in claim 1, wherein the inert liquid encapsulating polymer comprises a non-aqueous liquid encapsulating polymer.

23. The portable detection kit as in claim 1, wherein the dry reagent coated solid support article is formed into a strip.

24. The portable detection kit as in claim 1, wherein the solid support article is selected from the group consisting of glass, metal, paper, textiles, organic membranes, inorganic membranes, natural fibers, and synthetic fibers.

25. The portable detection kit as in claim 1, wherein the swab device comprises:
a handle; and
an absorbent matrix collection tip for surface sample collection and physical mixing of the suspect residue and the chemical reagent.

26. The portable detection kit as in claim 25, wherein the swab tip comprises absorbent synthetic or natural fibers.

27. The portable detection kit as in claim 25, wherein the swab tip comprises a dry tip.

28. The portable detection kit as in claim 25, wherein the swab tip comprises a tip pre-wetted with a solvent.

29. The portable detection kit as in claim 28, wherein the pre-wetted solvent comprises an aqueous solvent or an organic solvent.

30. The portable detection kit as in claim 29, wherein the organic solvent is selected from the group consisting of alcohols, acetone, chlorinated hydrocarbons, dimethyl sulfoxide, and organic acids.

31. The portable detection kit as in claim 29, wherein the aqueous solvent is selected from the group consisting of water, mineral acids and alkali.

32. The portable detection kit as in claim 1, wherein the package comprises a layer of a PET or cellulosic material, a layer of aluminum, and a layer of a Poly Ethylene material.

33. The portable detection kit as in claim 32, wherein:
the layer of a PET or cellulosic material is approximately 12 microns thick;
the layer of aluminum is approximately 7 microns thick; and
the layer of a Poly Ethylene material is approximately 50 microns thick.

34. A method of providing a portable detection kit for identifying the presence of a target narcotic, comprising:
mixing a homogenous suspension of a dry chemical powder reagent with an inert liquid encapsulating polymer;
depositing the encapsulated powder reagent onto a solid support article;
drying the encapsulated powder reagent;
pre-wetting a swab device with a solvent to facilitate the collection and transfer of a suspected residue to the reagent coated solid support article and upon contacting the narcotic residue with reagent coated solid support article and mixing all components together on the solid support article, a known visual colorimetric indication is produced thereby identifying a class of an unknown target narcotic present in the suspect residue; and
hermetically sealing the reagent coated solid support article and the swab device in a light, air, and moisture proof package prior to use.

35. The portable detection kit as in claim 34, wherein the target narcotic is selected from the group consisting of Amphetamine, Cannabis, Cocaine, Heroin, selected synthetic Cannabinoid and amphetamine based Cathinone type stimulants, and cannabis consumable products.

36. The method as in claim 34, further comprising mixing and homogenizing a plurality of powdered reagents in a laboratory ball, crusher, or shaker mill to produce the homogenous suspension of a dry chemical powder reagent.

37. The method as in claim 34, further comprising mixing the homogenous suspension of a dry chemical powder reagent with the inert liquid encapsulating polymer in inert mixing containers and high speed shaker beds or rotary impeller mixers.

38. The method as in claim 34, wherein depositing the encapsulated powder reagent onto the solid support article comprises an automated commercial printing process.

39. The method as in claim 38, wherein the commercial printing process is selected from the group consisting of letterpress, rotary gravure, screen printing, tampography, wax printing, contact dosing, ultrasonic sputter, and spray and drop on demand printing.

40. The method as in claim 34, wherein drying the deposited encapsulated powder reagent comprises a process selected from the group consisting of UV, IR, and hot air cure.

41. The method as in claim 34, further comprising forming the dry reagent coated solid support article into a predetermined shape by a process selected from the group consisting of injection molding, pressure forming, guillotining, and die-cutting.

42. The method as in claim 34, further comprising increasing long term chemical viability of the chemical reagent by a process selected from the group consisting of using inert liquid encapsulating suspension polymers, specific reagent mix combinations and ratios, physical separation of chemical reagents or mixtures of chemical reagents, and selective packaging.

43. The method as in claim 34, wherein depositing the encapsulated powder reagent comprises depositing a plurality of encapsulated powder reagents onto the solid support article separated by physical voids.

44. The method as in claim 34, further comprising hermetically sealing the dry reagent coated solid support article and the swab device in the package by vertical or horizontal form fill seal packaging systems.

45. The method according to claim 34, further comprising testing for the presence of a target narcotic by:
removing the dry reagent coated solid support and swab device from the sealed package;
rubbing an object with the swab device to transfer a molecule or ion of an unknown suspect residue from the object to the swab device;
contacting the swab device with the dry reagent on the solid support article to transfer the molecule or ion to the dry reagent powder; and
rubbing the swab device through the dry reagent powder on the solid support article to mix together the suspect residue, the dry reagent powder, and the swab wetting solvent;
whereby a chemical reaction is facilitated to produce a presumptive colorimetric indication of the presence of a target narcotic if a target narcotic is present.

* * * * *